(12) United States Patent
Andrews et al.

(10) Patent No.: US 8,834,156 B2
(45) Date of Patent: Sep. 16, 2014

(54) ORTHODONTIC BRACKET SYSTEM

(75) Inventors: Lawrence F. Andrews, San Diego, CA (US); Will A. Andrews, San Diego, CA (US)

(73) Assignee: Ortho Organizers, Inc., Carlsbad, CA (US)

(*) Notice: Subject to any disclaimer, the term of this patent is extended or adjusted under 35 U.S.C. 154(b) by 0 days.

(21) Appl. No.: 13/473,416

(22) Filed: May 16, 2012

(65) Prior Publication Data

US 2012/0295213 A1 Nov. 22, 2012

Related U.S. Application Data

(60) Provisional application No. 61/486,648, filed on May 16, 2011.

(51) Int. Cl.
*A61C 3/00* (2006.01)

(52) U.S. Cl.
USPC .............................................................. 433/9

(58) Field of Classification Search
USPC ........................................................ 433/8–16
See application file for complete search history.

(56) References Cited

U.S. PATENT DOCUMENTS

| | | | | |
|---|---|---|---|---|
| 5,160,261 A * | 11/1992 | Peterson | ............................ | 433/8 |
| 5,607,301 A * | 3/1997 | Roman | ............................. | 433/8 |
| 6,280,185 B1 * | 8/2001 | Palmer et al. | ....................... | 433/8 |
| 7,014,460 B2 * | 3/2006 | Lai et al. | ........................... | 433/11 |
| 7,131,836 B1 * | 11/2006 | Kesling | .............................. | 433/9 |
| 7,377,777 B2 * | 5/2008 | Lai et al. | ........................... | 433/11 |
| 2006/0024635 A1 * | 2/2006 | Lai | ................................... | 433/11 |
| 2007/0224568 A1 * | 9/2007 | Lin | ................................... | 433/8 |
| 2007/0281269 A1 * | 12/2007 | Forster | ............................. | 433/11 |

OTHER PUBLICATIONS notch. (n.d.). Dictionary.com Unabridged. Retrieved May 13, 2013, from Dictionary.com website: http://dictionary.reference.com/browse/notch.*
"Straight Wire, The Concept and Appliance." by Lawrence F. Andrews (L.A. Wells Co., 1989) Chapters 7-10 and 13: The Nonprogrammed Appliance, pp. 137-212; and 243-256.

* cited by examiner

*Primary Examiner* — Heidi M Eide
(74) *Attorney, Agent, or Firm* — Fulwider Patton LLP

(57) ABSTRACT

The orthodontic bracket system includes a bracket having a base for attachment to a tooth surface, a stem above the base, tie wings extending from the stem for securing ligatures, and an archwire slot for receiving an archwire defined by the stem and tie wings. Distal and mesial side surfaces of the bracket base are perpendicular to the archwire slot to allow a rotational device to apply rotational force to a tooth perpendicular to the archwire with direct vector-line guidance. Occlusal and gingival edges of the bracket base between the tie wings are scooped-out or recessed to provide more space to receive a tool under an elastic ligature, and select corners of the tie wings are beveled enlarging space to facilitate entry of instruments for removing wire ligatures, to facilitate instrument access for removal and replacement of ligatures, while streamlining tooth rotation to make arch correction more efficient.

3 Claims, 1 Drawing Sheet

US 8,834,156 B2

ORTHODONTIC BRACKET SYSTEM

CROSS-REFERENCES TO RELATED APPLICATIONS

This application is based upon and claims priority from Provisional Application No. 61/486,648, filed May 16, 2011, incorporated herein in its entirety.

BACKGROUND

This invention relates generally to brackets used in orthodontic treatment, and more particularly concerns orthodontic brackets having an archwire slot and that rely on ligatures to retain the archwire in the slot.

Orthodontic appliances, such as brackets, buccal tubes and the like are typically applied to teeth by adhering the appliances to the surface of the teeth to orient the teeth by the application of forces on the teeth by such orthodontic appliances. Such appliances typically include an archwire slot portion for receiving an archwire and ligatures, including elastic bands or metal/steel ligatures, to provide corrective forces to straighten and reposition the teeth. The orthodontic appliances typically include a base portion adapted generally to conform to the shape of the teeth to which they are applied, and elastic or wire ligature ties are used to hold the archwire in the archwire slot during initial and intermediate stages of treatment. However, installation and reinstallation of archwires in orthodontic brackets can be time consuming, and ligatures can become stained and may retain plaque and food debris, which can in turn result in tooth decay or infection. Accordingly, ligatures should be replaced regularly throughout the treatment period.

Conventional means of removing and replacing ligatures are time-consuming. The effects of such time consumption are multiplied since it is procedure required on most orthodontic patients multiple times throughout the treatment period.

There are six areas for which orthodontists have diagnostic responsibility. They are: Arch (Tooth Positions, Width, Shapes, and Length), AP (anteriorposterior) Jaw Positions, BL (buccolingual) Jaw Positions, SI (superiorinferior) Jaw Positions, Chin Prominence, and Occlusion. Of those six areas, the area that takes the most treatment time and effort is the correction of the Arch. Arch correction begins on the day the braces are placed and does not end until the day the braces come off. It is a constant battle between patient cooperation, skill of the orthodontist, treatment goals, appliance prescription, archwires, bracket positioning, and appropriate forces. Most orthodontists do not realize it but, how efficiently the arch is corrected is the major determinate of treatment time and office profitability.

It would be desirable to provide an orthodontic bracket system that reduces the time of ligature removal and replacement procedures. It would also be desirable to provide an orthodontic bracket system that facilitates improved rotational control of the tooth on which the bracket is placed with a rotational device. Such features would permit orthodontists to treat more patients per day and to correct patient arch problems more efficiently, thereby increasing the number of patients they are able to help while shortening treatment time and improving office profitability. The present invention meets these and other needs.

SUMMARY OF THE INVENTION

Briefly, and in general terms, the present invention provides for a direct vector-line tooth guidance system including orthodontic brackets having novel features that assist in rotational alignment of the tooth and expedite ligature removal and replacement. The configuration of the brackets is such that it is easier to manipulate orthodontic tools in the vicinity of the brackets to perform a desired objective, including ligature removal and rotation of the tooth.

Accordingly, the present invention provides for an orthodontic bracket, including a bracket body including a base configured to be attached to a surface of a tooth and a stem connected to and extending from the base, a plurality of tie wings extending from a surface of the stem in an occlusal or gingival direction, and an archwire slot or channel formed between the plurality of tie wings and defined along a surface of the stem, and configured to receive an archwire. The tie wings serve as support beams for securing ligatures, which are used to retain the archwire in position.

In a presently preferred aspect, one or more bevels are formed on a corner of each of the plurality of tie wings adjacent to the archwire slot, and are configured to provide space for access for use of wire cutters to access ligatures placed on or around the tie wings. In another presently preferred aspect, the plurality of tie wings have a substantially hook-shaped configuration configured for securing a ligature, and may be curved, and may be horizontally extended from both occlusal and gingival perspectives for ease of archwire ligation. In another presently preferred aspect, the one or more bevels are formed on each tie wing at a junction of the archwire slot and mesial borders of mesial ones of the tie wings and distal borders of distal ones of the tie wings. In another presently preferred aspect, the one or more bevels are formed on an outside corner of each of the plurality of tie wings. The outside corner may be a lower outside corner for a gingival side tie wing, or an upper outside corner for an occlusal side tie wing. Each tie wing of the bracket system may have a single bevel.

In another presently preferred aspect, the stem includes a cut out, scooped-out, or recessed portion on one or more of occlusal and gingival edges of the stem between opposing ones of the plurality of tie wings, and the recessed portion is preferably configured to provide space for use of an instrument to fit in between the plurality of tie wings to provide access to ligatures placed on or around the plurality of tie wings. In another presently preferred aspect, the recessed portion is formed between a distal side tie wing and a mesial side tie wing. In another presently preferred aspect, the recessed portion is formed on an occlusal side of the stem. In another presently preferred aspect, the recessed portion is formed on a gingival side of the stem. Accordingly, the present invention provides for improved access, removal, and replacement of both wire (metal or steel) and elastic ligature types.

In a presently preferred aspect, the stem comprises a first recessed portion on the stem on an occlusal side of the stem, and a second recessed portion on the stem on a gingival side of the stem. In another presently preferred aspect, the first recessed portion is positioned between a distal side tie wing and a mesial side tie wing. In another presently preferred aspect, the second recessed portion is positioned between a distal side tie wing and a mesial side tie wing. In another presently preferred aspect, the recessed portion extends into a portion of the archwire slot.

In another presently preferred aspect, the recessed portion extends onto the base. In another presently preferred aspect, a facial surface of the base includes recessed portions at occlusal and gingival edges of the base.

In one presently preferred aspect, distal and mesial surfaces of the stem are perpendicular to the archwire slot, whereby a rotational device can apply rotational force between a tooth and an archwire in the archwire slot for direct vector-line tooth guidance, potentially increasing patient comfort and shortening the treatment time period for arch correction. This geometry allows a rotational device to apply rotational force between the tooth and the archwire for direct vector-line tooth guidance, potentially increasing patient comfort and shortening the treatment time period for arch correction. In another presently preferred aspect, an occlusal surface of the stem is wedge-shaped, for less resistance to food during mastication resulting in fewer loose brackets.

In a further aspect, the present invention improves morphology of the bracket stem beneath the base. The base attaches directly to a surface of the tooth. Except for stems of 12-yr molar brackets, the mesial and distal surfaces of the bracket stems are angled so that they are perpendicular to the archwire slot. With this geometry, when rotation-spring auxiliaries are applied they will be at 90° to the archwire. Rotation devices for the teeth should be designed as the bracket is designed to ensure compatibility. The facial surface of the bracket base may be scooped at the occlusal and gingival edges to facilitate easy elastic removal.

These and other aspects and advantages of the invention will become apparent from the following detailed description, and the accompanying drawings which illustrate, by way of example, the features of the invention.

DETAILED DESCRIPTION OF THE PREFERRED EMBODIMENTS

Provided herein is an orthodontic bracket system that facilitates ligature access, removal and placement and also provisions for improved rotational control of teeth with a surface that accommodates a rotational device and leads to improving the rotational alignment process.

For elastic ligatures, the inter-tie wing cut out, scooped-out or recessed areas on both occlusal and gingival edges of the bracket stem create an opening for an instrument to be placed under the elastic ligature to aid in its removal.

For metal or steel ligatures, the bevels or notches on distal and mesial corners of the archwire slots creating spaces for beaks of wire cutters to access the metal or steel ligatures. Each tie wing has a single bevel. Each bracket has four tie wings and therefore there are four bevels for each bracket. The placement of the bevel on a tie wing is dependent on the position of the tie wing among the set of four tie wings on a bracket.

Figure 1:
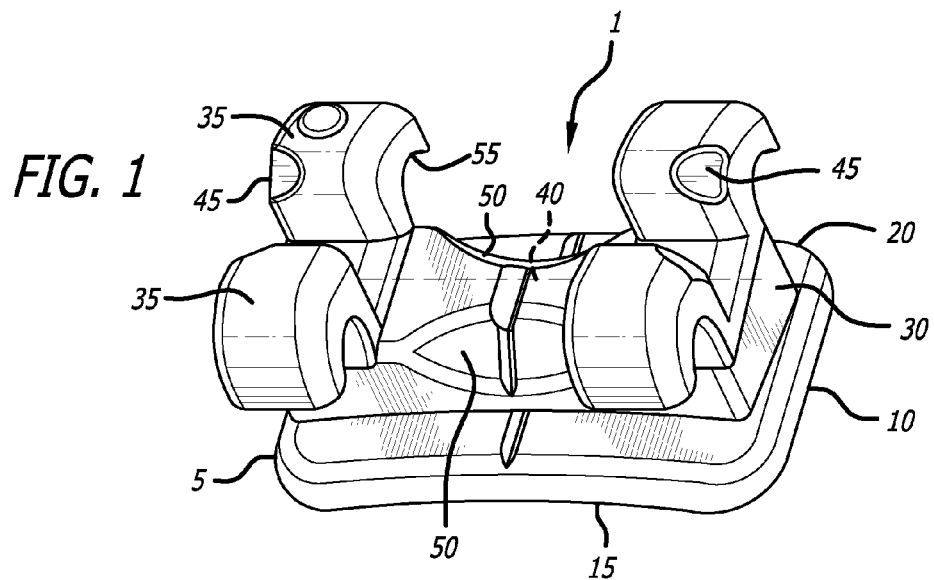
FIG. 1 is a perspective view of a bracket in accordance with the present invention.
Figure 3:
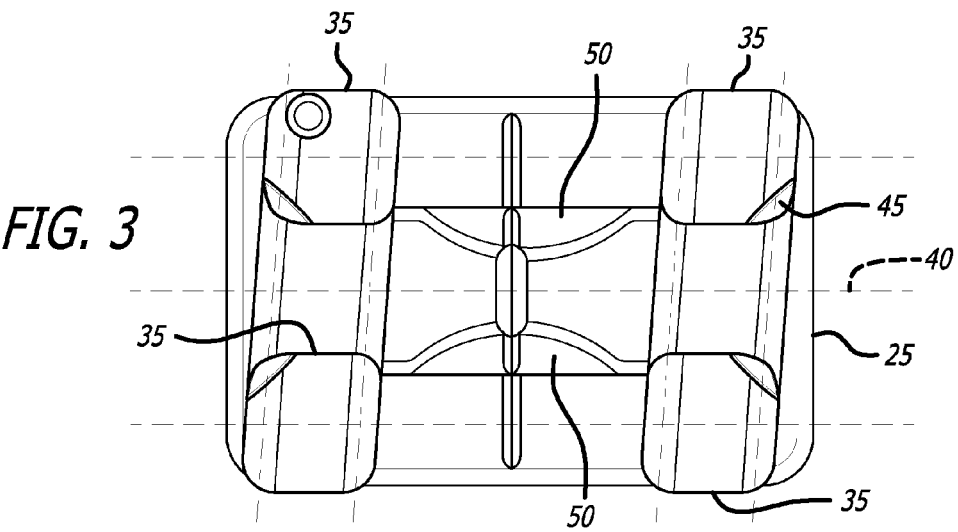
FIG. 3 is a plan view of a bracket in accordance with the present invention, showing the locations of the tie wing bevels.

Referring to FIGS. 1 and 3, for the upper left tie wing on a bracket the bevel is in the lower left corner. For the upper right tie wing on a bracket the bevel is in the lower right corner. For the lower left tie wing on a bracket the bevel is in the upper left corner. For the lower right tie wing on a bracket the bevel is in the upper right corner.

To improve rotational control of a tooth the bracket system has a bracket with a stem having distal and mesial side surfaces perpendicular to an archwire slot. This geometry permits a rotational device to apply rotational force to a tooth perpendicular to the archwire. Perpendicular application of a force is the most efficient use of force, is more comfortable for the patient, and shortens treatment time.

The stem of the bracket may also have distal and mesial side surfaces angled to be perpendicular to the archwire slot.

The distal tie wings of brackets may be horizontally extended (not illustrated). Horizontal extensions facilitate a new ligation method that eliminates having to negotiate around hooks or power arms. For brackets applied to six-year molars, both the distal and mesial tie wings may have horizontal extensions so that they can be ligated without having to negotiate around a gingival hook. The occlusal surfaces of the stems may be wedge-shaped for fending off food during mastication resulting in fewer debonded brackets (not illustrated).

The tie wings may also be curved from both occlusal and gingival perspectives to ease horizontal ligation.

The orthodontic bracket system provided herein offers solutions to arch correction not available elsewhere, providing direct vector-line tooth guidance that equates to treatment time reduction and enhanced profitability. Combined with the WALA Ridge concept, direct vector-line tooth guidance ensures each arch will be correctly shaped for better occlusion. The WALA Ridge is a band of soft tissue immediately superior to the muccogingival junction in the mandible. It is at or nearly at the same superior-inferior level as the horizontal center-of-rotation of the teeth. The WALA Ridge is the primary landmark for arch width and form and for archwire width and form.

The brackets for the orthodontic bracket system may include all of the features of Straight-Wire technology (See "Straight Wire, The Concept and Appliance" by Lawrence F. Andrews (L.A. Wells Co., 1989), including: (i) inclination in the base; (ii) compatible/interchangeable in/out prominence features; (iii) base point and slot point of the bracket are equal in distance from occlusal and gingival borders of brackets to allow the user to center the bracket on the crown face which causes the midtransverse and midsagittal planes of the crown and the bracket to superimpose, and the frontal planes of the crown and bracket to be parallel (See Chapters 8 & 9 of Straight Wire book) so that the archwire causes planes of the crown and slot to respond substantially simultaneously and equally.

Arch diagnosis informs the orthodontist which brackets set is most suitable (See Chapter 13 in Straight-Wire book). Standard brackets in accordance with one or more aspects of the present invention may be prescribed for teeth that need to be repositioned within their immediate boney area but not translated. Translational brackets in accordance with one or more aspects of the present invention should be prescribed for teeth that need both to be repositioned within their immediate boney area and also need to be translated. Translation brackets in accordance with one or more aspects of the present invention will align and translate teeth without archwire bends.

The brackets may be fully programmed or not fully programmed. The use of fully programmed brackets puts the burden of tooth and arch correction on the bracket manufacturer while the use of not fully programmed brackets puts the burden of tooth and arch correction on the orthodontist. Each bracket for each tooth type may have its own unique distance, or prominence, between the bracket's base point and the slot base so that the brackets will work together to eliminate in/out bends.

The brackets may be rhomboid in shape when viewed from the facial perspective. The occlusal, gingival, mesial, and distal edges of the slots, and the mesio/distal corners of the slots of all brackets may be beveled for ease of wire insertion and ligation removal. The contours of the bracket base may conform to the shape of the face of the crown for which the bracket is designed. According to one of several embodiments, the brackets have "Straight Wire" characteristics (as discussed in the book cited previously, see especially Chapters 8 & 9): inclination in base and planes of slots are extensions of planes of crowns.

When standard brackets are used with translational brackets the standard brackets should be 0.2 mm more prominent than they would otherwise have to be if no translational brackets were used. This additional prominence of the standard brackets used with translational brackets serves several important purposes: (i) it accommodates the anti-rotation feature needed in translation brackets; (ii) it allows standard brackets and translational brackets to be interchangeable; and (iii) it provides the stem space needed for the bracket to receive certain rotation devices. (See illustration 7.17 in Chapter 7 of the "Straight Wire" book cited previously.)

The stem of the bracket for molars, particularly 6 year molars, may be undercut to accommodate a rotation device. The undercut should be at the distal edge of the bracket to allow space on the distal side of the bracket for a rotation device to access the bracket. Preferably, the undercut is approximately 1.5 mm deep. Without the undercut there is typically not enough space between the distal edge of the bracket and the distal surface of the tooth to accommodate a rotation device. This is problematic because the 6 year molar is often the tooth that most needs to be rotated.

Ligation regions on the brackets should be generous. When necessary, stem height in the ligation area of mandibular brackets may be reduced to decrease the overall bracket height and to maximize the ligation region.

Referring to FIG. 1, an orthodontic bracket 1 is presented from a facial perspective as if on a surface of a tooth on a right side of a patient's mouth with the distal 5, mesial, 10, occlusal 15, and gingival 20 edges of the bracket illustrated. If the tooth shown was on a left side of a patient's arch instead, the distal and mesial sides would be reversed. Also shown are the basic elements of the bracket: the base 25, the stem 30, the tie wings 35, and the archwire slot 40. The tie wings 35 are curved 55.

Each of the four tie wings 35 of the bracket has a bevel or notch 45 in one of the four corners of the tie wing. The tie wing bevels are preferably positioned on the tie wings at distal and mesial corners of the bracket adjacent to the archwire slot. The bevels could also be described as being positioned on the vertically outer corners and horizontally inner corners of the tie wing as shown in FIG. 3. Whether this position for the bevel is the lower left, lower right, upper left, or upper right corner of the tie wing will depend upon which tie wing one is referring to and where that tie wing is positioned on the bracket. For example, for the upper left tie wing the bevel is in the lower left corner and for the lower right tie wing the bevel is in the upper right corner. Also shown are the inter-tie wing cut out, scooped-out or recessed portions 50 on both occlusal and gingival surfaces of the bracket stem 30. In a preferred aspect, the recessed portions extend onto a facial surface of the base, which may include recessed portions at occlusal and gingival edges of the base.

Figure 2:
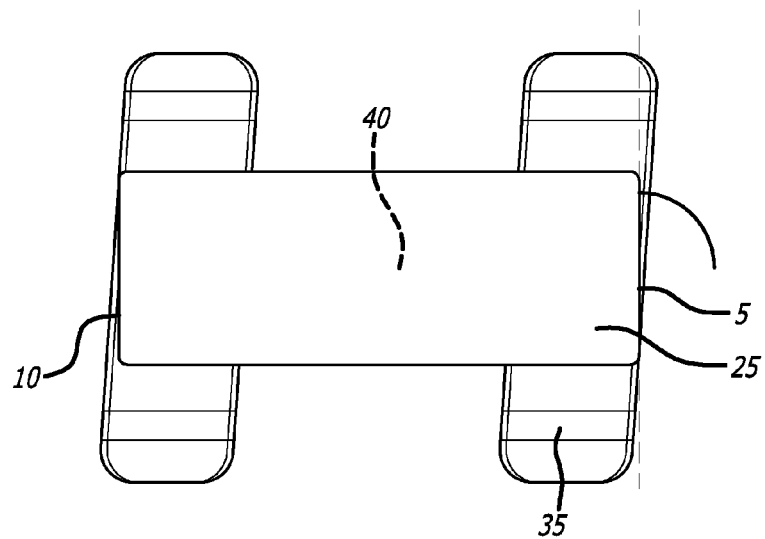
FIG. 2 illustrates a bracket stem perpendicular to the archwire slot.

Referring to FIG. 2, the view from underneath the bracket looking outward, as if outside of the mouth, shows how the bracket base 25 is perpendicular to the archwire slot 40 on both distal and mesial sides of the bracket base as shown for a bracket on a tooth on the right side of the mouth.

It will also be apparent from the foregoing that while particular forms of the invention have been illustrated and described, various modifications can be made without departing from the spirit and scope of the invention.

The invention claimed is:

1. An orthodontic bracket, comprising:
a bracket body including a base and a stem, said base being configured to be attached to a surface of a tooth, and said stem being connected to and extending from the base;
a plurality of tie wings extending from a surface of said stem in occlusal and gingival directions, said plurality of tie wings including opposing mesial tie wings and opposing distal tie wings;
an archwire slot having an axis formed between said plurality of tie wings and defined along a surface of said stem, said archwire slot being configured to receive an archwire, each of said opposing mesial tie wings having a corner at a junction of the archwire slot and mesial borders of said opposing mesial tie wings, and each of said opposing distal tie wings having a corner at a junction of the archwire slot and distal borders of said opposing distal tie wings, wherein distal and mesial surfaces of said stem are perpendicular to said archwire slot, said axis of said archwire slot is perpendicular to distal and mesial surfaces of said base, and said base is inclined with respect to said distal and mesial surfaces of said stem along said axis of said archwire slot; and
wherein a plurality of notches are formed on corresponding ones of said corners of said opposing mesial tie wings and corresponding ones of said corners of said opposing distal tie wings, respectively, adjacent to and extending into said archwire slot, said stem including a first scooped-out, recessed portion on an occlusal edge of said stem and a second scooped-out, recessed portion on a gingival edge of said stem, each of said first and second scooped-out, recessed portions extending a substantial majority of a distance between said opposing mesial tie wings and opposing distal tie wings, said first and second scooped-out, recessed portions extending into a portion of said archwire slot, said plurality of notches and said first and second scooped-out, recessed portions being configured to provide space for access for instruments to access ligatures placed on or around said plurality of tie wings.

2. The orthodontic bracket of claim 1, wherein said plurality of tie wings have a substantially hook-shaped configuration configured for securing a ligature.

3. The orthodontic bracket of claim 1, wherein said plurality of tie wings are curved.

\* \* \* \* \*